United States Patent [19]

Schiffert

[11] Patent Number: 4,703,263

[45] Date of Patent: Oct. 27, 1987

[54] METHOD FOR NON-DESTRUCTIVE TESTING OF A MAGNETIZABLE WORKPIECE UNDER COLD WEATHER CONDITIONS USING A MAGNETIC PARTICLE BATH

[75] Inventor: Phillip W. Schiffert, Oak Park, Ill.

[73] Assignee: Magnaflux Corporation, Chicago, Ill.

[21] Appl. No.: 761,357

[22] Filed: Aug. 1, 1985

[51] Int. Cl.$^4$ .................. G01N 27/84; G01R 33/12; G01M 27/82; H01F 1/28

[52] U.S. Cl. .................. 324/216; 324/215; 252/62.52

[58] Field of Search .................. 324/214–216; 252/62.52, 62.56

[56] References Cited

U.S. PATENT DOCUMENTS 3,609,532  7/1969  Vankirk et al. .................. 324/215
4,113,658  9/1978  Geus .................. 252/62.56
4,338,566  7/1982  Graham .................. 324/216

Primary Examiner—Reinhard J. Eisenzopf
Assistant Examiner—Walter E. Snow
Attorney, Agent, or Firm—J. P. O'Brien; T. W. Buckman

[57] ABSTRACT

A dry magnetic particle bath for non-destructive testing of a magnetizable workpiece to detect flaws comprising magnetic particles, a modified dextrose adhesive, and a carrier powder. In certain other embodiments of the invention the magnetic particle bath is instead a wet bath comprising water, magnetic particles, and modified dextrose. According to the invention, the wet bath can also contain an anti-freeze component consisting essentially of urea and ethylene glycol, glycerine or monoethanolamine to depress the freezing point of the water bath to 10°–15° F.; the invention encompasses wet bath formulations which contain the anti-freeze component in combination with adhesives other than modified dextrose.

31 Claims, No Drawings

METHOD FOR NON-DESTRUCTIVE TESTING OF A MAGNETIZABLE WORKPIECE UNDER COLD WEATHER CONDITIONS USING A MAGNETIC PARTICLE BATH

FIELD OF THE INVENTION

The field of this invention is non-destructive testing for flaws in a magnetizable workpiece utilizing an indicating composition in the form of a dispersion of magnetic particles.

BACKGROUND OF THE INVENTION

Application of magnetic particles in a fluid suspension, or in dry form, to a magnetized workpiece to detect flaws is a technique known in the art. According to that technique, the workpiece is magnetized, and then the magnetic particles are applied. Discontinuities or inhomogeneities in the workpiece which lie substantially transverse to the direction of the principal magnetic field cause the occurrence of localized leakage fields which capture some of the magnetic particles. Collections of these particles held by the leakage fields form patterns which reveal the existence and locations of the discontinuities and inhomogeneities.

In a more recent development magnetic particles have been combined with a fluorescent pigment to aid in detection of discontinuity- or inhomogeneity-caused patterns after the magnetic particles have been applied to the magnetized workpiece. A further development is the encapsulation of adherent fluorescent pigment and magnetic particles in a coating of film-forming resin, as disclosed in U.S. Pat. No. 3,485,758, naming as inventors James S. Borucki and Paul Kenneth Borrows, granted Dec. 23, 1969, and assigned to Magnaflux Corporation.

The magnetic particle inspection method described above is employed commercially to detect flaws in relatively large ferromagnetic bodies. One of the principal areas of its utilization is in the inspection of steel billets. Flaws such as seams in those billets result from any of a large number of causes, some mechanical and some metallurgical. Typical examples are removal of metal from the steel surface by scaring or scaling; formation of strings of non-metallic inclusions; formation of metallic inclusions which have a different permeability from the parent metal; the occurrence of overfill or underfill in the rolls during hot or cold working operations; and formation of cold shuts due to an overlapping of the metal resulting from splashing in the mold during ingot formation. It is particularly important to locate seams which are longitudinal discontinuities in such billets; those seams appear as light lines in the surface of the steel. They are normally closed tight enough so that no actual opening can be visually detected, thus making magnetic particle inspection necessary.

However, several distinct problems and disadvantages accompany use of conventional magnetic particle inspection techniques, especially as regards steel billets. Those billets are normally inspected in a continuous process in which each billet travels at relatively high velocity (for example, about 120 feet per minute) through a magnetizing field, and then through an applicator station where fluorescent-type magnetic particles are applied.

Conventional methods for application of magnetic particles in dry form onto the billet have the inherent shortcoming that under some conditions the magnetic particles do not come to complete equilibrium on the magnetized billet in the short time allotted due to the high speed of handling; that precludes formation of patterns corresponding to smaller inhomogeneities and discontinuities in the steel billet and prevents their detection. A further requirement of dry application which can be disadvantageous is that the billets must be pre-heated at least to room temperature. Nevertheless, for some jobs dry application is an acceptable and convenient technique.

But, even when they might otherwise be acceptable, conventional dry application techniques are not always satisfactory. That state of affairs results from the fact that a dry magnetic particle bath normally contains a binder agent which fixes the magnetic particles in the bath to the workpiece. The binder agents ordinarily employed - such as resins, waxes, and even in some instances sodium silicate - are not insubstantial in their contribution to the overall cost of formulating the bath, and difficulties in obtaining some of those agents can also add expense and inconvenience. Furthermore, a number of conventionally employed binders are incompatible with post-inspection practices, and are difficult to remove from the workpieces when the need to preserve the flaw-indications formed by clustered magnetic particles has passed.

The wet method eliminates some of the problems attendant on dry application and thus is more suitable for use under conditions which make dry bath application less desirable. But the wet method also has certain drawbacks under some conditions encountered in commercial operation.

While the use of oil for suspending magnetic particles has the advantage of dissolving any oily film on the surface of the workpiece to be tested, the oil suspension impedes drying, and thus affixation, of the magnetic particles on the billet. Throughout the inspection process, the billet is likely to be handled roughly with the result that the collections of magnetic particles at seams and other flaws may be disturbed or even destroyed. Further, the oil bath can present a potential fire hazard depending on the means used to magnetize the workpiece.

Thus, in the testing of larger workpieces, and especially steel billets, utilization of a water bath is favorable due to lower costs and the complete elimination of bath flammability. That bath conventionally contains a wetting agent—for example a non-ionic wetting agent such as ethoxylated nonylphenol—to aid in dispersing the magnetic particles on the billet so that the bath can spread evenly over its entire surface. The bath frequently contains an adhesive, such as a resin, wax or sodium silicate, which acts as a binder to fix the magnetic particles on the workpiece upon drying or evaporation of the bath liquid. The adhesive minimizes the chance that magnetically formed indications will be disturbed by jostling of the workpiece during handling prior to inspection.

However, conventional water baths have the disadvantage that they cannot be used when the temperature drops below freezing unless the bath and/or workpiece are pre-heated, a measure which results in processing difficulties and economic loss. Use of anti-freeze components in the water bath is generally not feasible because the quantities needed to be effective would raise the viscosity of the bath above the maximum allowable. High bath-viscosity slows the movement of particles under the influence of the magnetic field. At viscosities above about five Centistokes, the movement of magnetic particles in the bath is sufficiently retarded to have a definite effect in reducing the build-up, and therefore the visibility, of patterns of magnetic particles at small discontinuities in the workpiece.

Indeed, the anti-freeze component ethylene glycol when actually employed by itself has exhibited just such disadvantageous behavior, becoming viscous at low temperatures and decreasing the mobility of the magnetic particles in suspension. Moreover, ethylene glycol by itself impedes drying of the bath liquid after application on the workpiece and thus prevents affixation of the magnetic particles on the workpiece. Rather, a slushy film is formed on the workpiece which is often disadvantageously removed during handling of the workpiece prior to its inspection for flaws. Yet another disadvantage of ethylene glycol is that it insolubilizes the adhesive. (Other known anti-freeze components such as alcohol and sodium chloride, if present in more than 8% by volume, will also precipitate the adhesive out of solution.)

It can thus be readily appreciated that provision of magnetic particle bath, and inspection method, embodiments which confer on the art the advantages of magnetic particle testing using either a dry or water-base bath, but eliminate the previously discussed problems, would be a highly desirable advance over the current state of technology.

OBJECTS OF THE INVENTION

It is an object of this invention to provide a magnetic particle bath containing an adhesive component which, when applied to a workpiece, yields a continuous, transparent, non-fluorescent film securely fixing the magnetic particles to the workpiece.

It is a second object of this invention to provide a magnetic particle bath containing an inexpensive adhesive component which yields an adhesive film (on the workpiece) which is easily removed with water.

It is an additional object of the invention to provide a method for non-destructive testing of a ferromagnetic workpiece which enables dry application of a magnetic particle bath to obtain a formation on the workpiece exhibiting the aforementioned beneficial properties.

It is also an object of the invention to provide a magnetic particle water bath for use at temperatures near or below freezing, which bath does not require its pre-heating or that of the workpiece to be tested, the bath containing an anti-freeze component which depresses the bath's freezing point to a suitably low temperature, for instance, 10°–15° F.

It is a further object of this invention to provide a magnetic particle water bath containing an anti-freeze component which is compatible with an included adhesive, does not react with that adhesive and does not cause the adhesive to precipitate out.

It is an additional object of this invention to provide a magnetic particle water bath containing an anti-freeze component which enables low-temperature formation of particle-indications at flaws before the particles are immobilized.

It is another object of this invention to provide a magnetic particle water bath containing an anti-freeze component which does not impede drying of the bath on the workpiece.

It is still another object of this invention to provide a magnetic particle bath containing an anti-freeze component which does not prevent affixation of the magnetic particles on the workpiece.

Yet another object of this invention is to provide a method for the non-destructive testing of steel billets and other magnetizable workpieces at low temperatures utilizing a magnetic particle water bath containing an anti-freeze component such that pre-heating of the billets or the water bath is obviated and yet the other objects and advantages described above are attained.

These and other objects and advantages of the present invention will become more readily apparent after consideration of the following.

STATEMENT AND ADVANTAGES OF THE INVENTION

In one aspect the present invention is directed to a magnetic particle bath for use in non-destructive testing of a magnetizable workpiece, which comprises magnetic particles, modified dextrose, and a carrier powder.

In a further aspect, the invention relates to a method for non-destructive testing of a magnetizable workpiece, which comprises magnetizing the workpiece, applying to it a magnetic particle bath containing magnetic particles, modified dextrose and a carrier powder, fixing the magnetic particles to the workpiece, and inspecting the workpiece for flaws indicated by the presence of clusters of magnetic particles on its surface.

In an additional aspect the present invention is directed to a magnetic particle bath for non-destructive testing of a magnetizable workpiece, which comprises magnetic particles, water, an adhesive, a wetting agent and an anti-freeze component comprising urea in combination with one or more of ethylene glycol, monoethanolamine and glycerine.

In another aspect, the invention is directed to a concentrate composition suitable for formulation of such magnetic particle water bath, which composition comprises magnetic particles, an adhesive, a wetting agent, and an anti-freeze component comprising urea in combination with ethylene glycol, monoethanolamine or glycerine.

In yet another aspect, the invention is directed to a method for non-destructive testing of a magnetizable workpiece, which comprises magnetizing the workpiece, applying to it a magnetic particle bath containing water, magnetic particles, an adhesive, a wetting agent and an anti-freeze component consisting essentially of urea and at least one other constituent selected from the group consisting of ethylene glycol, glycerine and monoethanolamine; fixing the magnetic particles to the workpiece by evaporation of the liquid component of the bath; and inspecting the workpiece for flaws indicated by the presence of clusters of magnetic particles on its surface.

In still another aspect, the invention is directed to a method for non-destructive testing of a magnetizable workpiece, which comprises magnetizing the workpiece; applying to the magnetized workpiece a magnetic particle water bath comprising fluorescent magnetic particles, water, a wetting agent, an adhesive comprising modified dextrose, and an anti-freeze component compatible with that adhesive comprising urea in combination with ethylene glycol, monoethanolamine or glycerine; fixing the fluorescent magnetic particles to the workpiece by evaporation of the liquid component of the bath; and inspecting the workpiece for flaws indicated by the presence of clusters of the magnetic particles on its surface.

Numerous advantages accrue with the practice of the present invention.

The employment of modified dextrose as an adhesive component in a bath used for magnetic particle testing, regardless of whether the bath is wet or dry, confers a valuable economy and convenience on the invention's practitioners. It forms a continuous, transparent, non-fluorescent lacquer film when used as an adhesive (or binder). In contrast to other adhesives (or binders), such as resins, waxes and water glass, the material is both inexpensive and readily obtainable. While (as those skilled in the art will appreciate) a modified dextrose adhesive does not provide abrasive resistance of the degree provided by a water glass adhesive, in many instances the excellent resistance of modified dextrose adhesive to magnetic particle indication displacement more than compensates. Furthermore, a modified dextrose adhesive is easily removed with water after inspection and is thus an important advance over those conventional adhesive components which are difficult to remove and incompatible with post-inspection practices. Additionally, it is advantageous that modified dextrose is neutral in water and not highly caustic as at least one other conventional binder is.

Similarly, the incorporation in a magnetic particle water bath of urea in combination with at least one of ethylene glycol, monoethanolamine and glycerine is advantageous in that it acts as a freezing point depressant, and further advantageous because it does not unacceptably increase the viscosity of the magnetic particle bath. Also, drying of the magnetic particle bath on the billet proceeds acceptably. Furthermore, the combination anti-freeze component permits affixation of the magnetic particles on the billet sufficiently that the billet may be handled without detrimentally disturbing or removing the magnetic particles. Additionally, urea, ethylene glycol, monoethanolamine and glycerine are not volatile, and are miscible with water; their use thus affords significant processing economics.

Moreover, the modified dextrose adhesive and the anti-freeze component comprising urea in combination with ethylene glycol, monoethanolamine or glycerine are particularly compatible with one another when used in a magnetic particle water bath. This can be seen from the facts that the anti-freeze component does not detrimentally interfere with the fixation of the indications by the modified dextrose adhesive, and that the anti-freeze combination does not appreciably react with the adhesive or cause it to insolubilize from the water bath.

Thus, the invention provides a magnetic particle bath, and method of utilizing same for non-destructive testing by magnetic particle inspection, ideally suited for operation at low temperature. In the following section the invention is described in greater detail to illustrate several of its especially advantageous embodiments.

DESCRIPTION OF CERTAIN PREFERRED EMBODIMENTS

The concentration of suspended magnetic particles in the bath varies in relation to the intended use and desired effect. The guide to proper bath concentration is the formation of satisfactory indications. A reliable method of assuring optimum bath concentration for any given combination of equipment, bath application, type of workpiece and defects sought to be identified, is to determine acceptable bath concentrations preliminarily by using parts with known defects. Bath strength can be adjusted by cut-and-try methods until satisfactory indications are obtained. This concentration of bath can then be adopted as standard for those conditions.

Typical examples of magnetic particles which can be employed are magnetic iron oxide, carbonyl iron or a soft magnetic ferrite. However, while any conventionally employed magnetic particle is suitable, it is often advantageous to use fluorescent magnetic particles, preferably those having a magnetic core over which is coated a fluorescent pigment, the coating being attached to the core by an encapsulating resin. Such fluorescent magnetic particles are described in U.S. Pat. No. 3,485,758 previously discussed and U.S. Pat. No. 4,341,997, naming as the inventor Kenneth P. Borrows, granted July 27, 1982 and assigned to Magnaflux Corporation. The entire subject matter of each of those patents is hereby incorporated by reference.

The magnetic particles used are preferably of a size ranging from 40 to 70 microns in maximum dimension, and fluorescent dye particles (if employed) are typically fine-sized, illustratively ranging from 2 to 10 microns in maximum dimension.

When using fluorescent pigment particles, magnetic particle content also depends on the average particle size. For example, particles can be used at a certain concentration for particles of 5 micron average diameter, at twice that concentration for particles averaging 30 to 40 microns in diameter, and from two to four times that first concentration for very coarse particles. The variation occurs because finer particles contain many more particles per unit of weight, and weight concentrations thus need not be as high.

The proportion of magnetic particles in the bath is preferably maintained at a uniform level. If the concentration varies, the strength of indication also varies, and indications may be misinterpreted. Faint indications resulting from use of a weak bath may be missed entirely. Too heavy a concentration of particles resulting from use of a very strong bath can give a confusing background and excessive adherence of particles at external poles, thus interfering with clean-cut indications of extremely fine flaws.

In certain advantageous embodiments of the invention, a cascading opacifier component is included in a fluorescent magnetic particle bath. That opacifier component has the property of absorbing rays in the ultraviolet region with the emission of additional visible light over and above what would be reflected if the substance were submitted to visible light radiation only. Suitable opacifier components are discussed in further detail in U.S. Pat. No. 4,338,566 naming as the inventor Bruce C. Graham, granted July 6, 1982 and assigned to Magnaflux Corporation. All of the subject matter of that patent is hereby incorporated by reference.

As previously indicated, the advantages conferred by the present invention extend both to application of dry bath compositions and wet bath compositions.

In those embodiments of the invention in which the magnetic particle bath is applied in dry form, the bath itself comprises a suspension of the aforementioned magnetic particles in a fluidizing bath of a light, non-sticking carrier powder.

The carrier powder is suitably any appropriately sized particulate material which does not react with any other of the bath components or with water. Typical carrier powders are composed of alumina aerogel and/or silica aerogel, a light fluffy inert powder with a bulk density of about 3 to 8 lb/ft$^3$, particle diameters around 0.02 microns and a large surface area; a silica aerogel (available commercially as the product Santocel C from Monsanto, Cab-O-Sil M5 from Cabot Laboratories and Tullanox from Tulco, Inc., for instance) is preferred; a hydrated alumina aerogel carrier powder formed of finely sized aluminum oxide particles (available commercially as the product named Alon C from Degussa, for instance) is especially preferred.

Also included in such composition is a modified dextrose component. Modified dextrose is a malto-dextrin product composed primarily of high molecular weight saccharides with a small amount of dextrose and maltose formed by hydrolyzing corn starch; it does not absorb moisture, is essentially non-deliquescent and is highly water-soluble. Modified dextrose is widely available in the industry, and can be obtained in commercial form from several different sources. One typical example of suitable material is sold by American Maize-Products Co. under the trade names Lowdex-10 and Fro-Dex.

The modified dextrose component is incorporated in the bath system in an amount sufficient to effect affixation of the magnetic particles. In a particularly advantageous embodiment of the invention the modified dextrose binder component is deposited directly on the surfaces of the magnetic particles prior to their application to a workpiece. This is suitably accomplished by mixing the magnetic particles, for instance IR-10 Iron Powder, with an aqueous solution of Lowdex-10—and if desired a water-dispersed fluorescent pigment—and then rapidly introducing isopropyl alcohol. Since the dextrose material is highly soluble in water, but insoluble in isopropyl alcohol, the introduction of the alcohol causes the dextrose material to come out of solution and be deposited on the magnetic particles. If fluorescent pigment is present it is also attached to the magnetic particles during the aforementioned processing. The resulting mass is dried, then ground to obtain the fluorescent magnetic particles. Of course, it will be appreciated that the modified dextrose material can also be attached, by means of the above-mentioned processing, to premanufactured fluorescent magnetic particles such as Magnaflux Corporation's MG-400 material.

The dry bath normally contains about 60 to 80% by weight of modified dextrose-bearing magnetic particles with the balance of about 20 to 40% by weight being the carrier powder. Of course, if the modified dextrose is not bound to the magnetic particles but incorporated in the dry bath as a separate component, it will make up an amount of the bath suitable to achieve the desired binding (adhesive) effect - say on the order of about 20 to 40% by weight. The amount of magnetic particle component will be correspondingly reduced.

In operation, the aforementioned dry bath is sprayed or poured onto a workpiece which, along the way, is magnetized. Magnetization can be accomplished by any convenient means. For example, the workpiece can be subjected to the magnetic field of, or brought into contact with, a permanent magnet. Alternatively, and preferably in most situations, the workpiece is magnetized by the passage of current through a solenoid either wrapped around the workpiece, or around a fixed frame with which the workpiece is contacted or otherwise brought into association. The flaw indications resulting from migration of the magnetic particles are set by exposure of the bath-coated workpiece to water vapor, e.g., steam, which causes the modified dextrose binder component to become tacky. Examination can then be conducted at an appropriate time.

Turning to the embodiments of the invention wherein a wet bath is applied to the workpiece, it is advantageous that the bath contain magnetic particles in an amount of from 1/10 to ¼ ounce per gallon of final bath. It is especially preferred that the magnetic particle bath contains such particles in an amount of from 1/5 to ¼ ounce per gallon of final bath.

In the practice of wet bath embodiments in which the modified dextrose binder described previously is employed, it is often advantageous to form a concentrated solution of the modified dextrose component, typically about 30 to 50% by weight of the modified dextrose. That concentrated solution is then added to an aqueous magnetic particle bath until the bath contains on the order of 35 to 60% by volume of dextrose solution and 65 to 40% by volume of water plus normal bath components, as further indicated hereinafter. In an alternative, and also frequently advantageous, embodiment modified dextrose powder can be combined with a wetting agent (one of the normal bath components to be described infra) and that combination added directly to a magnetic particle bath. The wetting agent is generally employed in powder form, and used in a small amount, often a fraction of a percent (by weight). The bath is made up so that it preferably contains 4 to 30%, especially 8 to 20%, by weight of modified dextrose. While preferred amounts of modified dextrose amounts are disclosed in the foregoing discussion, it will be understood that other amounts of that component are also suitable as long as they are sufficient to effect affixation of the magnetic particles.

The wet magnetic particle baths of the invention suitably contain one or more additional bath components. One such additional component is a surfactant or wetting agent. Because fluorescent magnetic particles normally have a hydrophobic surface, it is desirable to lower the water's surface tension to achieve fast wetting of the magnetic particles to facilitate formation of indications on the billet. Thus a surfactant or wetting agent is included in an amount sufficient to effect the amount and rate of wetting desired. Any known non-ionic wetting agent is suitable. Illustratively, when the magnetic particles are used at a concentration of about 1/10 ounce per gallon, the following compositions can be utilized in a bath which is sprayed onto the workpiece:

Ethoxylated nonylphenol (surface active agent, 0.01–0.02% by weight);

Dow Corning "Antifoam A" (0.004–0.007%);

Borax (0.004–0.06%). The borax can be substituted in whole or in part by calcium acetate, calcium propinate, or sodium benzoate. The wetting agent is preferably included in an amount ranging from 1/10 to ¼ ounce per gallon of final bath, especially 1/10 to ⅛ ounce per gallon of final bath.

Additionally, when using a modified dextrose component it is advantageous to include 100 to 500 ppm (of the final bath) of a biocide such as acetyl trimethyl amonium chloride.

A further component, the incorporation of which in a magnetic particle water bath constitutes another significant aspect of the invention, is an anti-freeze component comprising urea in combination with ethylene glycol, monoethanolamine or glycerine. In this regard, the present invention extends beyond employment of such anti-freeze component in magnetic particle water baths containing a modified dextrose adhesive (or binder); it is within the scope of the invention to employ the antifreeze component in baths which instead contain other materials which function as adhesives (binders), particularly sodium silicate. The component is included in the bath in an amount sufficient to attain the required freezing point depression for the bath, but not in an amount so great that viscosity, drying and other desired properties are sacrificed. An amount of from 10 to 40 percent by volume of the final bath is preferred, and especially 15 to 25 volume percent. The relative proportion of urea to ethylene glycol, monoethanolamine or glycerine is preferably from 10:1 to 1.5:1, especially 8:1 to 4:1.

In utilizing the magnetic particle water bath, the method of the invention provides ready means for effective and reliable detection of flaws in magnetizable workpieces under cold-weather conditions, as described above.

The wet baths discussed herein may be formulated by combining their components (including water) by any convenient technique, for instance admixing. All of those components can be combined directly, or instead in stages by preparing a concentrate from which all or most of the water necessary to form the magnetic particle water bath is omitted and then adding water and any other previously omitted components to the concentrate at an appropriate time or times. The components of the concentrate are, of course, incorporated in amounts designed to yield the desired chemistry in a magnetic particle bath ultimately formulated. A concentrate composition along the foregoing lines provides a convenient form in which to transport or store materials suitable for practicing the invention, and is a useful precursor which can be diluted as necessary to yield a fresh bath, thereby constituting a particularly advantageous embodiment of this invention.

To practice the inventive method embodiments in which a wet bath is employed, the workpiece is magnetized by any convenient method, such as one of those discussed previously herein. The bath is applied to the magnetized workpiece by spraying, or by immersion or dipping of the workpiece in the bath, or by pouring of the bath over the workpiece - or by any other technique adequate to effect thorough coating of the workpiece. Magnetic particles are held to defects by the magnetic leakage field. Then, the magnetic particles are fixed by evaporating the liquid component of the bath on the workpiece. By way of example, this can be accomplished by exposing the bath-coated workpiece to a heated air stream of moderate velocity and/or by drying in the ambient atmosphere. Upon drying of the inspected surface, the adhesive, especially the modified dextrose binder, forms a thin, continuous film. The film is concentrated at the sites of defects due to the wetted surface area of the individual magnetic particles. This film holds the magnetic particles in place during normal handling until such time as the defects are resolved. In due course the workpiece is inspected, for instance by simple visual examination or with the aid of fluorescent light, for the occurrence of clusters of magnetic particles indicating the existence and location of flaws.

According to one operational embodiment, the workpiece to be inspected is passed through a standard magnetizing yoke of the type used in magnetic particle inspection processes. Then, the magnetic particle water bath is sprayed onto the surface of the billet. Any residual water is removed by means of a hot air blast. The billet is then inspected (for instance while being irradiated with ultraviolet light and normal white light) for clusters of the fluorescent magnetic particles.

Further objects of this invention, together with additional features contributing thereto and advantages accruing therefrom, will be apparent from the following examples of the invention.

EXAMPLE 1

A dry magnetic particle bath was formulated containing 40 pounds fluorescent magnetic particles, 40 pounds Lowdex-10 modified dextrose and 20 pounds silica aerogel carrier powder. The bath was applied to a magnetized workpiece by pouring of the bath over the workpiece. The magnetic particles were fixed on the workpiece by exposing the bath-coated workpiece to steam. Magnetic particle indications were successfully fixed after their formation at discontinuities and the modified dextrose adhesive was easily removed with water after inspection.

EXAMPLE 2

A magnetic particle water bath was prepared containing 20 ounces fluorescent magnetic particles, 165 pounds Lowdex-10 modified dextrose, 12 ounces wetting agent containing tetramethyl decynediol and nonionic ethoxylated $C_{13}$—$C_{16}$ alcohols having from 5 to 12 ethylene oxide groups, 100 gallons water and ½ ounce trimethyl octadecyl amonium chloride biocide. The bath was applied to a magnetized workpiece by spraying of the bath onto the workpiece. The magnetic particles were fixed on the workpiece by exposing the bath-coated workpiece to a heated air stream to evaporate the liquid component of the bath on the workpiece. Magnetic particle indications were successfully fixed after their formation at discontinuities and the modified dextrose adhesive was easily removed with water after inspection.

EXAMPLE 3

A magnetic particle water bath was formulated containing 13.5% by volume urea and 3% by volume monoethanol amine as the anti-freeze component and 10% by volume modified dextrose binder.

The freezing point of the bath was depressed to 19° F. and the viscosity of the bath was acceptably low.

The bath was applied to a magnetized workpiece by spraying of the bath onto the workpiece. The magnetic particles were fixed on the workpiece by exposing the bath-coated workpiece to a heated air stream to evaporate the liquid component of the bath on the workpiece. The magnetic particle indications were successfully fixed after their formulation at discontinuities with only a slight increase in drying time over that of an analogous bath without the added urea and monoethanol amine.

EXAMPLE 4

A magnetic particle water bath was prepared containing 13.5% by volume urea and 8% by volume monoethanol amine as the anti-freeze component and 10% by volume modified dextrose binder.

The freezing point of the bath was depressed to 14° F. The bath was applied to a magnetized workpiece and the magnetic particles were fixed on the workpiece as in Example 3. The bath readily dried, its viscosity was acceptably low and the magnetic particle indications were successfully fixed.

EXAMPLE 5

A magnetic particle bath was prepared containing 15% by volume urea and 6% by volume glycerine as the anti-freeze component and 15% by volume modified dextrose binder.

The freezing point of the bath was depressed to 15.5° F. The bath was applied to a magnetized workpiece and the magnetic particles were fixed on the workpiece as in Example 3. The bath readily dried and magnetic particle indications were successfully fixed.

EXAMPLE 6

A magnetic particle bath was prepared containing 15% by volume urea and 8% by volume glycerine as the anti-freeze component and 15% by volume modified dextrose binder.

The freezing point of the bath was depressed to 14° F. The bath was applied to a magnetized workpiece and the magnetic particles were fixed on the workpiece as in Example 3. The bath readily dried and magnetic particle indications were successfully fixed.

EXAMPLE 7

A magnetic particle bath was prepared containing 13.5% by volume urea and 7% by volume ethylene glycol as the anti-freeze component and 15% by volume modified dextrose binder.

The freezing point of the bath was depressed to 13.5° F. The bath was applied to a magnetized workpiece and the magnetic particles were fixed on the workpiece as in Example 3. The bath readily dried and magnetic particle indications were successfully fixed.

EXAMPLE 8

A magnetic particle bath was prepared containing 13.5% by volume urea and 9% by volume ethylene glycol as the anti-freeze component and 15% by volume modified dextrose binder.

The freezing point of the bath was depressed to 11.5° F. The bath was applied to a magnetized workpiece and the magnetic particles were fixed on the workpiece as in Example 3. The bath readily dried and magnetic particle indications were successfully fixed.

EXAMPLE 9

A magnetic particle bath was prepared containing 17% by volume urea and 3% by volume monoethanol amine as the anti-freeze component and 10% by volume modified dextrose binder.

The freezing point of the bath was depressed to 17° F. The bath was applied to a magnetized workpiece and the magnetic particles were fixed on the workpiece as in Example 3. The bath readily dried and magnetic particle indications were successfully fixed.

EXAMPLE 10

A magnetic particle bath was prepared containing 17% by volume urea and 8% by volume monoethanol amine as the anti-freeze component and 10% by volume modified dextrose binder.

The freezing point of the bath was depressed to 11° F. The bath was applied to a magnetized workpiece and the magnetic particles were fixed on the workpiece as in Example 3. The bath readily dried and magnetic particle indications were successfully fixed.

EXAMPLE 11

A magnetic particle bath was prepared containing 13.5% by volume urea and 3% by volume monoethanol amine as the anti-freeze component and 15% by volume modified dextrose binder.

The freezing point of the bath was depressed to 17° F. The bath was applied to a magnetized workpiece and the magnetic particles were fixed on the workpiece as in Example 3. The bath readily dried and magnetic particle indications were successfully fixed.

EXAMPLE 12

A magnetic particle bath was prepared containing 13.5% by volume urea and 8% by volume monoethanol amine as the anti-freeze component and 15% by volume modified dextrose binder.

The freezing point of the bath was depressed to 11° F. The bath was applied to a magnetized workpiece and the magnetic particles were fixed on the workpiece as in Example 3. The bath readily dried and magnetic particle indications were successfully fixed.

EXAMPLE 13

A magnetic particle bath was prepared containing 17% by volume urea and 3.25% by volume monoethanol amine as the anti-freeze component and 15% by volume modified dextrose binder.

The freezing point of the bath was depressed to 15° F. The bath was applied to a magnetized workpiece and the magnetic particles were fixed on the workpiece as in Example 3. The bath readily dried and magnetic particle indications were successfully fixed.

COMPARATIVE EXAMPLE 14

A magnetic particle water bath was prepared containing 22.8% by volume urea not in combination with ethylene glycol, monoethanol amine or glycerine.

The freezing point of the bath was depressed to 17.5° F. and the viscosity of the bath upon the addition of urea was reasonably low.

The bath was applied to a magnetized workpiece by spraying of the bath onto the workpiece. The magnetic particles were fixed on the workpiece by exposing the bath-coated workpiece to a heated air stream to evaporate the liquid component of the bath on the workpiece. The bath readily dried but formed a rather slushy deposit which indicated an unacceptable tendency to resist particle-fixation on a workpiece.

While the invention has been described with reference to specific examples, it will be understood by those skilled in the art that a range of chemistries may be employed and equivalents may be substituted for elements thereof without departing from the scope of the invention. The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. A dry magnetic particle bath for use in non-destructive testing of a magnetizable workpiece, which comprises magnetic particles, modified dextrose, and a carrier powder.

2. A magnetic particle bath as defined in claim 1, wherein the modified dextrose is deposited on the surface of the magnetic particles and the dextrose-bearing magnetic particles constitute from 60 to 80 weight % of the bath.

3. A magnetic particle bath as defined in claim 1, wherein the modified dextrose constitutes 20 to 40 weight % of the bath.

4. A magnetic particle bath as defined in claim 1, wherein the carrier powder constitutes 20 to 40 weight % of the bath.

5. A magnetic particle bath as defined in claim 4, wherein the carrier powder is finely-sized aluminum oxide particles.

6. A magnetic particle bath as defined in claim 1, wherein the magnetic particles are fluorescent magnetic particles.

7. A method for non-destructive testing of a magnetizable workpiece, which comprises magnetizing the workpiece, applying to it a magnetic particle bath containing magnetic particles, modified dextrose and a carrier powder, fixing the magnetic particles to the workpiece, and inspecting the workpiece for flaws indicated by the presence of clusters of magnetic particles on its surface.

8. A method as defined in claim 7, wherein the modified dextrose constitutes 20 to 40 weight % of the bath.

9. A method as defined in claim 7, wherein the modified dextrose is deposited on the surface of the magnetic particles and the dextrose-bearing particles constitute from 60 to 80 weight % of the bath.

10. A method as defined in claim 7, wherein the carrier powder constitutes 20 to 40 weight % of the bath.

11. A method as defined in claim 10, wherein the carrier powder is finely-sized aluminum oxide particles.

12. A method as defined in claim 7, which comprises contacting the bath-covered workpiece with water vapor and evaporating the water to fix the magnetic particles.

13. A method as defined in claim 7, wherein the magnetic particles are fluorescent magnetic particles.

14. A magnetic particle bath suitable for non-destructive testing of a magnetizable workpiece under cold-weather conditions, which comprises water, magnetic particles, modified dextrose as an adhesive component, a wetting agent, and an anti-freeze component consisting essentially of urea and ethylene glycol, glycerine or monoethanolamine.

15. A magnetic particle bath as defined in claim 14, which comprises an amount of said anti-freeze component effective to preserve the composition's fluidity at a temperature as low as 15° F.

16. A magnetic particle bath as defined in claim 14, which further comprises a biocidal agent.

17. A magnetic particle bath as defined in claim 14, wherein the magnetic particles are fluorescent magnetic particles.

18. A magnetic particle bath suitable for non-destructive testing of a magnetizable workpiece under cold-weather conditions, which comprises water, magnetic particles, an adhesive, and an anti-freeze component consisting essentially of urea and ethylene glycol, glycerine or monoethanolamine.

19. A magnetic particle bath as defined in claim 18, wherein the adhesive is sodium silicate.

20. A magnetic particle bath as defined in claim 18, wherein the magnetic particles are fluorescent magnetic particles.

21. A magnetic particle bath as defined in claim 18, which comprises 1/10 to ¼ ounce of magnetic particles per gallon of the bath, 1/10 to ⅛ ounce of wetting agent per gallon of the bath, 4 to 30 volume percent adhesive and 10 to 30 volume percent of said anti-freeze component.

22. A method for non-destructive testing of a magnetizable workpiece under cold-weather conditions, which comprises magnetizing the workpiece; applying to it a magnetic particle bath containing water, magnetic particles, an adhesive, a wetting agent and an anti-freeze component consisting essentially of urea and ethylene glycol, glycerine or monoethanolamine; fixing the magnetic particles to the workpiece by evaporation of the liquid component of the bath; and inspecting the workpiece for flaws indicated by the presence of clusters of the magnetic particles on its surface.

23. A method as defined in claim 22, wherein an amount of said anti-freeze component effective to preserve the composition's fluidity at a temperature as low as 15° F. is present.

24. A method as defined in claim 22, wherein the magnetic particles are fluorescent magnetic particles.

25. A method as defined in claim 22, wherein the adhesive is sodium silicate.

26. A method as defined in claim 22, wherein the bath contains 1/10 to ¼ ounce of magnetic particles per gallon of the bath, 1/10 to ⅛ ounce of wetting agent per gallon of the bath, 4 to 30 volume percent adhesive and 10 to 30 volume percent of said anti-freeze component.

27. A concentrate composition suitable for formulation of a magnetic particle water bath for non-destructive testing of a magnetizable workpiece under cold-weather conditions, which comprises magnetic particles, an adhesive, a wetting agent, and an anti-freeze component consisting essentially of urea and ethylene glycol, glycerine or monoethanolamine.

28. A concentrate composition as defined in claim 27, which comprises an amount of said anti-freeze component effective to preserve the fluidity, at a temperature as low as 15° F., of a magnetic particle water bath made therefrom.

29. A concentrate composition as defined in claim 27, wherein the magnetic particles are fluorescent magnetic particles.

30. A concentrate composition as defined in claim 27, wherein the adhesive is sodium silicate.

31. A concentrate composition as defined in claim 27, wherein the amounts of magnetic particles, adhesive, wetting agent and anti-freeze component are such that a magnetic particle water bath ultimately formulated from the composition contains 1/10 to ¼ ounce of magnetic particles per gallon of the bath, 1/10 to ⅛ ounce of wetting agent per gallon of the bath, 4 to 30 volume percent adhesive and 10 to 30 volume percent of said anti-freeze component.

* * * * *